United States Patent
Du et al.

(10) Patent No.: US 10,208,088 B1
(45) Date of Patent: Feb. 19, 2019

(54) LOW MOLECULAR POLYPEPTIDE ZY4 AND APPLICATIONS THEREOF

(71) Applicant: Sichuan Synlight Biotech Ltd., Chengdu (CN)

(72) Inventors: Yanjun Du, Chengdu (CN); Dafu Zeng, Chengdu (CN)

(73) Assignee: SICHUAN SYNLIGHT BIOTECH LTD., Chengdu (CN)

( * ) Notice: Subject to any disclaimer, the term of this patent is extended or adjusted under 35 U.S.C. 154(b) by 0 days.

(21) Appl. No.: 15/580,694

(22) PCT Filed: Jan. 12, 2016

(86) PCT No.: PCT/CN2016/070739
§ 371 (c)(1),
(2) Date: Dec. 8, 2017

(87) PCT Pub. No.: WO2016/201972
PCT Pub. Date: Dec. 22, 2016

(30) Foreign Application Priority Data

Jun. 15, 2015 (CN) .......................... 2015 1 0331263

(51) Int. Cl.
| | | |
|---|---|---|
| *A61K 38/10* | (2006.01) |
| *C07K 7/08* | (2006.01) |
| *A61P 17/10* | (2006.01) |
| *A61P 35/00* | (2006.01) |
| *A61P 31/10* | (2006.01) |
| *A61K 47/10* | (2017.01) |
| *A61P 31/04* | (2006.01) |
| *A61K 38/00* | (2006.01) |

(52) U.S. Cl.
CPC .............. *C07K 7/08* (2013.01); *A61K 38/10* (2013.01); *A61K 47/10* (2013.01); *A61P 17/10* (2018.01); *A61P 31/04* (2018.01); *A61P 31/10* (2018.01); *A61P 35/00* (2018.01); *A61K 38/00* (2013.01)

(58) Field of Classification Search
None
See application file for complete search history.

(56) References Cited

FOREIGN PATENT DOCUMENTS

| | | |
|---|---|---|
| CN | 102924574 A | 2/2013 |
| CN | 103275190 A | 9/2013 |
| CN | 104623628 A | 5/2015 |
| CN | 104974228 A | 10/2015 |

OTHER PUBLICATIONS

Bahar, Ali Adem and Ren, Dacheng, "Antimicrobial peptides." Pharmaceuticals (2013) 6 p. 1543-1575.*

* cited by examiner

*Primary Examiner* — Fred H Reynolds
(74) *Attorney, Agent, or Firm* — Gokalp Bayramoglu

(57) ABSTRACT

The present invention discloses the applications of a low molecular polypeptide ZY4 in preparing drugs for anti-*acnes*, anti-infection, anti-cancer and cosmetics. The low molecular polypeptide ZY4 comprises 17 amino acid residues, with a molecular weight of 2374.0 Da, an isoelectric point of 10.74, and an amino acid sequence of SEQ ID NO:1. The low molecular polypeptide ZY4 in the invention is artificially synthesized, with the advantages of small molecular weight and convenient artificial synthesis. The experiments have showed that the polypeptide ZY4 has obvious antibacterial effect and has significant therapeutic effect on *acnes*. The polypeptides can inhibit the growth of tumor cells and kill the tumor cells. The low molecular polypeptide ZY4 can be used in the preparation of medicaments or cosmetics having the effect of anti-infective, anti-tumor or anti-acne.

7 Claims, 7 Drawing Sheets

Specification includes a Sequence Listing.

LOW MOLECULAR POLYPEPTIDE ZY4 AND APPLICATIONS THEREOF

CROSS REFERENCE TO RELATED APPLICATIONS

This application is the national phase entry of International Application No. PCT/CN2016/070739, filed on Jan. 12, 2016, which is based upon and claims priority to Chinese Patent Application No. CN201510331263.5, filed on Jun. 15, 2015, the entire contents of which are incorporated herein by reference.

TECHNICAL FIELD

The present invention belongs to the technical field of biomedicine, specifically, it relates to the applications of low molecular polypeptide ZY4 in preparing drugs for anti-*acnes* and anti-infection and anti-cancer as well as cosmetics.

BACKGROUND OF THE INVENTION

Acne is a chronic inflammation of hair follicles sebaceous glands, and it is a common inflammatory skin disease in adolescence, frequently occurring in the cheeks, forehead, and nasolabial fold, followed by the chest, back and shoulders. Its incidence is mainly associated with the sex hormone level, large sebaceous secretion, *P. acnes* proliferation, keratinization of hair follicle sebaceous duct and inflammation. During adolescence, the skin lipid components have changed, and the androgen increases, resulting in hyperkeratosis of sebaceous follicle duct, mixture of epithelial cells and sebum in the hair follicle wall to form embolism in the hair follicles and *acnes*. When affected with propionibacteria and bacterial infection, it will cause inflammation and produce abscess, making patients very painful.

When the body is affected by various carcinogenic factors, the growth of a cell in local tissue may not be normally regulated at the gene level, which results in clonal abnormal proliferation and forms a tumor. Tumors are divided into two types: benign and malignant tumors according to their harms to human body and growth characteristics. Malignant tumors grow rapidly and often infiltrate the adjacent tissues when growing, without envelop on the surface, and accompanied by systemic metastasis. At present, the incidence of malignant tumors has been increasing year by year which is a major reason of deaths in various diseases; therefore, the prevention and treatment are very important.

Antimicrobial peptide is a kind of bioactive low molecular polypeptide induced in vivo. Its molecular weight is about 1000~7000. The antimicrobial peptide consists of 10~60 amino acid residues. Antimicrobial peptide is an efficient and broad-spectrum antimicrobial peptide molecules quickly produced by the body when an organism is invaded by microorganisms, to involve in the body's immune response. Antimicrobial peptides widely exist as effective defensive molecules in the body. At present, thousands of antimicrobial peptides have been identified from microorganisms, plants, insects, arthropods, amphibians, mammals and even humans. The antimicrobial mechanism of antimicrobial peptides is complex, but most of theories consider that its mechanism involves the cationic and hydrophobic properties of antimicrobial peptides and the actions with the negatively charged microbial cell membrane; and when antimicrobial peptides contact with bacterial cell membranes, it will cause changes in membrane permeability, or form a transmembrane hole on the bacterial cell membrane, finally resulting in the leakage of bacterial contents and death. As a result, antimicrobial peptides are much stronger in killing bacteria than traditional antibiotics, and unlike antibiotics, which inhibit bacterial growth at low concentrations, antimicrobial peptides are almost fatal to bacteria. The results show that compared with traditional antibiotics, antimicrobial peptides do not readily induce the antibacterial spectra by the drug-resistant strains. It can produce effects on bacteria, fungi, viruses, protozoa and cancer cells. Three families of antimicrobial peptides have been found in poultry, including cathelicidin, liver-expressed antimicrobial peptide (LEAP), and β-defensin. These antimicrobial peptides are crucial for poultry's resistance to bacterial and viral diseases. Mutations or deletions of these genes will have a significant impact on the ability of poultry to resist microbial infection. In addition to broad-pectrum antibacterial activity, these antimicrobial peptides are highly effective against fungi, viruses, protozos and/or tumors, for example, Bat5 and Mc7 can kill *Leptospira, Candida albicans, Cryptococcus* and membrane viruses and parasites; some antimicrobial peptides have obvious killing effect on Herpes virus, influenza virus, HIV and enveloped virus. In addition, some antimicrobial peptides also have a variety of other regulatory functions, for example, Cathelicidin has the functions of prompting wound healing, tissue damage repair, chemotaxis, pro-angiogenesis and anti-parasites, etc., having has important biological activity in regulating animal body immunity.

SUMMARY OF THE INVENTION

An object of the present invention is to overcome the defects of the prior art and provide a low molecular polypeptide ZY4;

Another object of the present invention is to provide applications of low molecular polypeptide ZY4 in preparing drugs for anti-*acnes* and anti-infection and anti-cancer as well as cosmetics.

The present invention is achieved through the following technical solutions: a low molecular polypeptide ZY4, comprising 17 amino acid residues, with a molecular weight of 2374.0 Da, an isoelectric point of 10.74, and its amino acid sequence is as shown in SEQ ID: 1: Valine-Cysteine-Lysine-Arginine-Tryptophan-Lysine-Lysine-Tryptophan-Lysine-Arginine-Lysine-Tryptophan-Lysine Lysine-Tryptophan-Cysteine-Valinamide. Two Cysteines in the gene sequence form an intramolecular disulfide bond and the C-terminal Val is amidated.

The low molecular polypeptide ZY4 in the invention is used in the preparation of anti-acne, anti-infective, anti-tumor medicaments and cosmetics.

The invention can achieve the following beneficial effects: The low molecular polypeptide ZY4 in the invention is artificially synthesized, with the advantages of small molecular weight and convenient artificial synthesis. The experiments have showed that the polypeptide ZY4 has obvious antibacterial effect and has significant therapeutic effect on *acnes*. The polypeptides can inhibit the growth of tumor cells and kill the tumor cells; and the low molecular polypeptide ZY4 can be used in the preparation of anti-infective, anti-tumor and anti-acne medicaments and cosmetics.

DETAILED DESCRIPTIONS OF THE INVENTION

Figure 1:
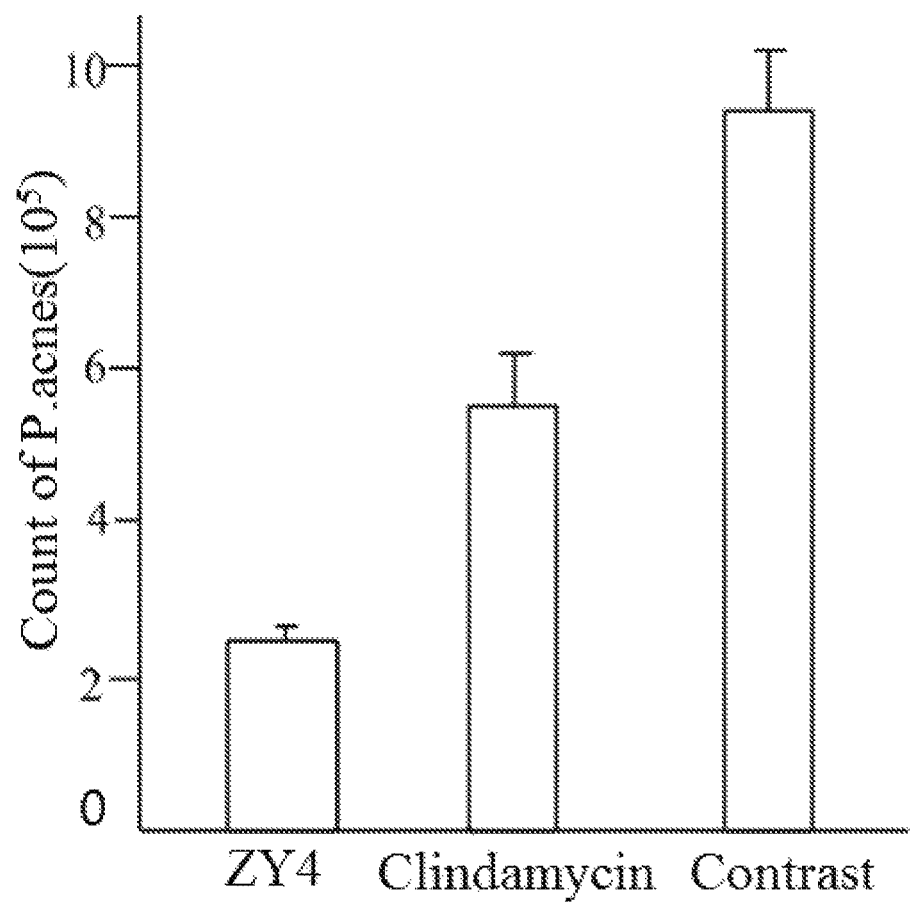
FIG. 1 is a schematic diagram of the therapeutic effect of low molecular polypeptide ZY4 on mouse ear acne models.

The present invention is further described below with reference to the accompanying drawings and embodiments. The protection scope of the present invention is not limited to the following:

Embodiment 1: Preparation of Low Molecular Polypeptide ZY4

1. Weigh 0.2 g of resin and place to a dry and clean reaction tube, add appropriate amount of N, N-dimethyl formamide (DMF) for activation 30 min. Weigh 1 mmol of first amino acid residue and 150 mg of 4-dimethylamino pyridine (DMAP) to the reaction tube, to react 3 h using DMF as solvent; after the reaction, wash with DMF for 3-6 times, add appropriate amount of pyridine and acetic anhydride at a volume ratio of 1:1, to react 30 min, and after the reaction, wash with DMF for 3-6 times. Then the amino acid protecting group Fmoc is eluted with piperidine twice, 15 min each time, and then washed with DMF for 4 times, and washed with methanol twice;

2. Weigh 3 mmol of second amino acid and 3 mmol of HBTU in a reaction tube, add 0.5 ml of DIEA, to react 40 min, then wash with DMF for 3-6 times. Add piperidine solution twice to elute the amino acid protecting group Fmoc, 10 min each time, and then wash with DMF for 4 times, and wash with methanol twice;

3. Repeat the second step until the last amino acid residue;

4. After the reaction of the last amino acid, cut with trifluoroacetic acid 2 h for suction filtration, to get the polypeptide in trifluoroacetic acid solution, then precipitate with ether and centrifuge, and wash with ether for 3-5 times, to get a white solid, and then desalt and lyophilize through HPLC, to get the polypeptide samples.

Embodiment 2: Antibacterial Experiment of Low Molecular Polypeptide ZY4

1. Prepare *Escherichia coli, Candida albicans, Staphylococcus aureus, Bacillus subtilis, Staphylococcus haemolyticus, Staphylococcus epidermidis, Staphylococcus cohnii* solutions respectively, incubate at 37° C. for 18 h, for standby;

2. Prepare low molecular polypeptide ZY4 solution at a concentration of 0.8-20 ug/ml. Disinfect and dry the circular qualitative filters with a diameter of 5-7 mm, and then immerse them into the low molecular polypeptide ZY4 solution at different concentrations;

3. Prepare Broth Agar Medium, and sterilize it for standby;

4. Dissolve the Broth Agar Medium, cool down to 50° C., add 1 ml of *Escherichia coli, Candida albicans, Staphylococcus aureus, Bacillus subtilis, Staphylococcus haemolyticus, Staphylococcus epidermidis, Staphylococcus cohnii* solutions respectively, shake gently and pour into a sterile petri dish, gently shake the medium to evenly pave on the dish;

5. Place the filters into a cooled dish using a sterile tweezer orderly, cover with a tile cover and mark, then place to a 37° C. incubator for incubation for 24 h;

6. Measure the size of inhibition zone with a caliper, and compare the effect of low molecular polypeptide ZY4 at different concentrations on different bacteria. Results are shown in Table 1 and Table 2.

TABLE 1 effect of the low molecular polypeptide ZY4 at different concentrations on different bacteria

| Microorganisms | Minimum inhibitory concentration (ug/ml) |
|---|---|
| *Escherichia coli* | 12.15 |
| *Candida albicans* | 2.12 |
| *Staphylococcus aureus* | 2.14 |
| *Bacillus subtilis* | 1.10 |

As shown from Table 1, the minimum inhibitory concentrations of low molecular polypeptide ZY4 on *Escherichia coli, Candida albicans, Staphylococcus aureus* and *Bacillus subtilis* are 12.15 ug/ml, 2.12 ug/ml, 2.14 ug/ml, and 1.10 ug/ml respectively.

TABLE 2 effect of the low molecular polypeptide ZY4 at different concentrations on different bacteria

| Microorganisms | Minimum inhibitory concentration (ug/ml) |
|---|---|
| *Staphylococcus aureus* (09B2499) | 2.25 |
| *Staphylococcus haemolyticus* (09A4394 anti-ampicillin) | 2.17 |
| *Staphylococcus epidermidis* (09A3726 anti-ampicillin) | 2.45 |
| *Staphylococcus cohnii* (09B2490 anti-ampicillin) | 1.10 |

As shown from Table 2, the minimum inhibitory concentrations of low molecular polypeptide ZY4 on *Staphylococcus aureus, Staphylococcus haemolyticus, Staphylococcus epidermidis, Staphylococcus cohnii* related to acnes are 2.25 ug/ml, 2.17 ug/ml, 2.45 ug/ml and 1.10 ug/ml respectively. The experimental results show that the low molecular polypeptide ZY4 has a significant inhibitory effect.

Embodiment 3: Therapeutic Effect of Low Molecular Polypeptide ZY4 on Mouse Ear Acne Models 1. Culture *P. acnes* ATCC11817 with brain heart infusion agar until the logarithmic phase, wash twice with normal saline (NS) and resuspend to $5\times10^8$ CFU/ml with NS;

2. Select Kunming male mice at a weight of 18 g each, and randomly divide them into 3 groups, 6 mice each group, respectively the treatment group, positive control group, negative control group. Each mouse is anaesthetized with 120 ul of 1% pentobarbital sodium by intraperitoneal injection, and then injected with 20 ul of resuspended bacteria solution via intracutaneous injection in the left ear of each mouse;

3. Prepare the low molecular polypeptide ZY4, clindamycin into 2 mg/ml ointments using PEG and glycerol respectively (the weight ratio of PEG to glycerol is 5:1), smear them on the left ear skin of the mice. In the treatment group, mice are smeared with low molecular polypeptide ZY4, in the positive control group, mice are smeared with clindamycin, and in the negative control group, mice are smeared with PEG, once every 8 h, for 3 times in total, 24 h later, mice are sacrificed;

4. Disinfect the left ears of mice with a clean alcohol cotton ball, cut off the left ears into pieces, transfer to a homogenizer for homogenization. Add 1 ml of NS for homogenization for one ear;

5. Dilute the homogenate to 1,000-fold, take 50 ul of diluent and apply to a brain heart infusion agar plate, culture at 37° C. under the anaerobic condition for 72 h, and count the colonies. The results are shown in FIG. 1. The CFU of $P.$ $acnes$ after treatment with 2 mg/ml low molecular polypeptide ZY4 is $2.1 \times 10^5$, the CFU of $P.$ $acnes$ after treatment with 2 mg/ml of clindamycin is $5.6 \times 10^5$, and the CFU of $P.$ $acnes$ after treatment with PEG is $9.44 \times 10^5$, suggesting that ZY4 has a better therapeutic effect on mice ear $acnes$ than clindamycin.

Figure 2:
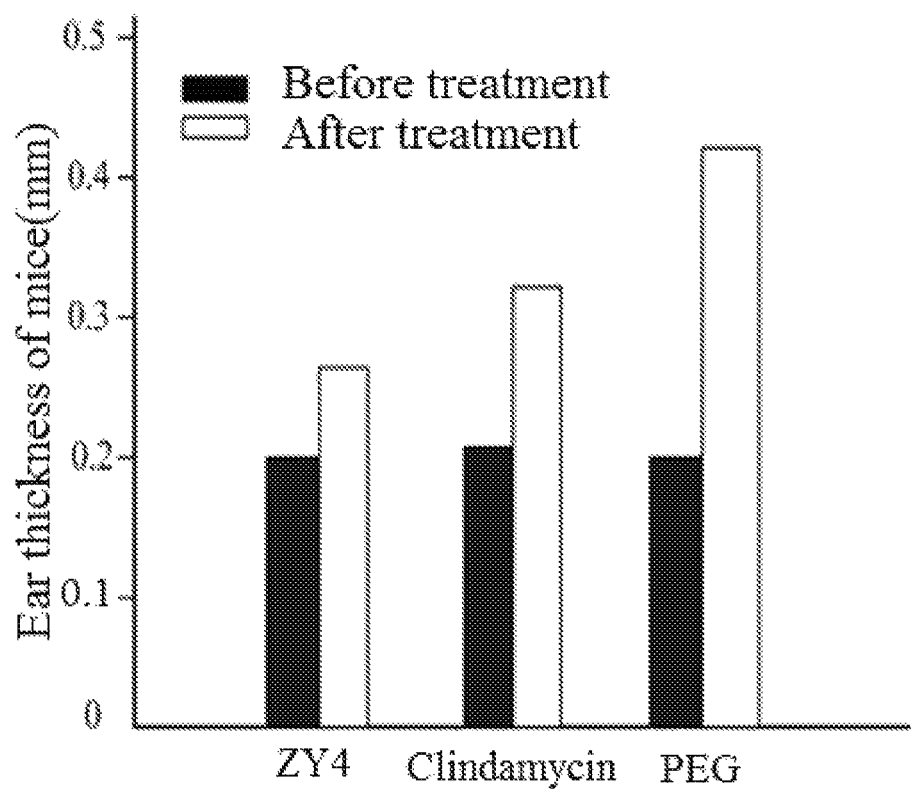
FIG. 2 is a schematic diagram of the therapeutic effect of low molecular polypeptide ZY4 on inflammations of mouse ear acne models.

Embodiment 4: Therapeutic Effect of Low Molecular Polypeptide ZY4 on Inflammations of Mouse Ear Acne Models 1. Culture $P.$ $acnes$ ATCC6919 with brain heart infusion agar until the logarithmic phase, wash twice with normal saline (NS) and resuspend to $5 \times 10^8$ CFU/ml with NS;

2. Select Kunming male mice at a weight of 18 g each, and randomly divide them into 3 groups, 9 mice each group, respectively the treatment group, positive control group, negative control group. Each mouse is anaesthetized with 50 ul of ketamine by intraperitoneal injection, and then injected with 20 ul of resuspended bacteria solution via intracutaneous injection in the left ear of each mouse;

3. Prepare the low molecular polypeptide ZY4 and clindamycin into 2 mg/ml ointments using PEG and glycerol respectively (the weight ratio of PEG to glycerol is 5:1), smear them on the left ear skin of the mice. In the treatment group, mice are smeared with low molecular polypeptide ZY4, in the positive control group, mice are smeared with clindamycin, and in the negative control group, mice are smeared with PEG, once every 8 h, for 3 times in total, 24 h later, mice are sacrificed;

4. Disinfect the left ears of mice with a clean alcohol cotton ball, and measure the thickness of the ears of mice, results are shown in FIG. 2. The thickness of mice ear is 0.20 mm before treatment. After treated with 2 mg/ml low molecular polypeptide ZY4 for 1 day, the thickness of mice ear is 0.25 mm; after treated with 2 mg/ml of clindamycin for 1 day, the thickness of mice ear is 0.34 mm, and after treated with PEG for 1 day, the thickness of mice ear is 0.43 mm, suggesting that ZY4 has a better inflammatory effect than clindamycin.

Embodiment 5: Assay on Activity of Low Molecular Polypeptide ZY4 Against Lung Cancer Cell A549

Figure 3:
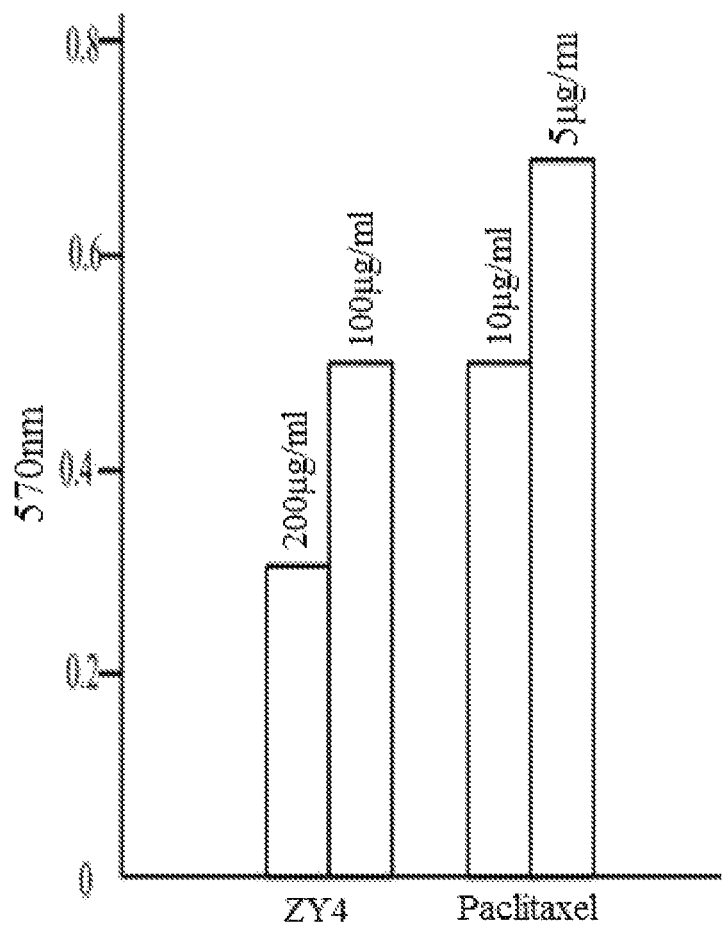
FIG. 3 is a schematic diagram of anti-lung cancer cell A549 activity of low molecular polypeptide ZY4.

1. Collect the lung cancer cell A549 in the logarithmic phase to prepare cell suspension, adjust its concentration to $5 \times 10^6$-$10 \times 10^6$/ml, add 100 ul to each hole, pave the plate to adjust the cell density to 1000-10000 holes; fill the holes on the edges with sterile PBS;

2. Incubate cells under the condition of 5% CO2 and 37° C. until the cell monolayer are paved on 96-hole plate bottom; after cell adhesion for 2-12 h, add the low molecular polypeptide ZY4 at a concentration of 100 ug/ml and 200 ug/ml, paclitaxel at a concentration of 10 ug/ml and 5 ug/ml to incubate for 16-48 h under the condition of 5% CO2 and 37° C., and then observe under an inverted microscope;

3. Add 20 ul of 5 mg/ml MTT solution to each hole, to continue to culture 4 h, and then draw the culture solution in the hole;

4. Add 150 ul of DMSO to each hole, place to a shaker for oscillation 10 min at a low speed, to allow the crystals fully dissolved, measure the absorbance values of each hole at OD 490 nm using a ELISA Reader; at the same time, set the zero hole and control hole. Results are shown in FIG. 3. The OD value is 0.3 when lung cancer cells A549 are treated by 200 ug/ml ZY4; and OD value is 0.5 when lung cancer cells A549 are treated by 100 ug/ml ZY4; OD value is 0.5 when lung cancer cells A549 are treated by 10 ug/ml paclitaxel; and OD value is 0.7 when lung cancer cells A549 are treated by 10 ug/ml paclitaxel, suggesting that ZY4 has a significant inhibitory effect on lung cancer cell A549.

Embodiment 6: Assay on Activity of Low Molecular Polypeptide ZY4 Against Breast Cancer Cell MDA-435

Figure 4:
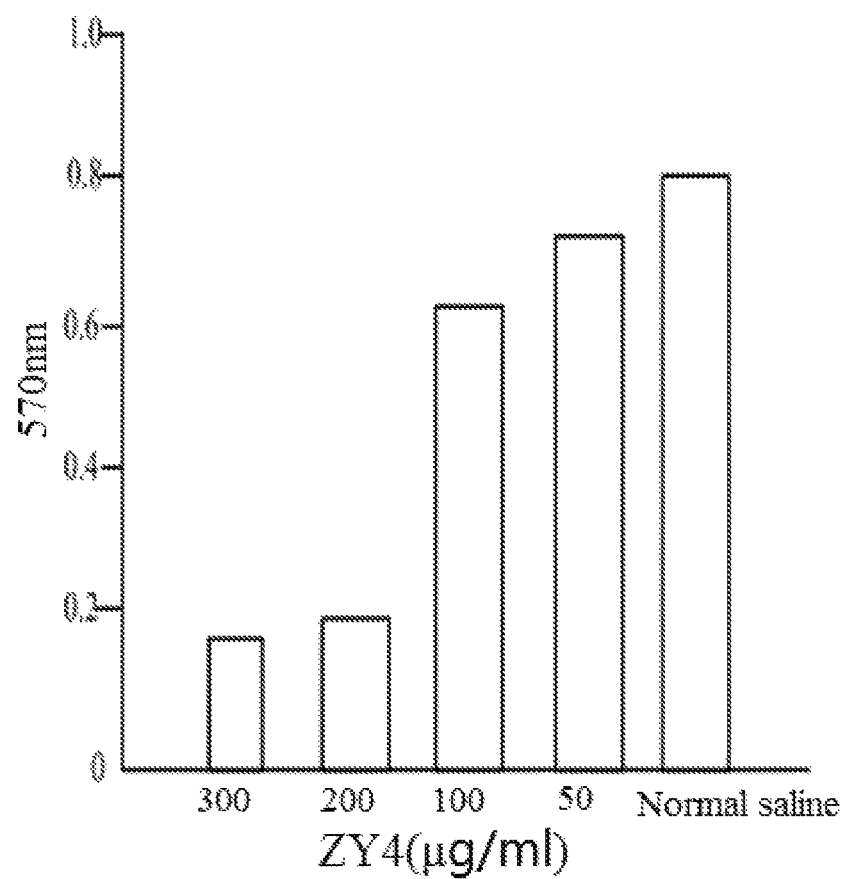
FIG. 4 is a schematic diagram of anti-breast cancer cell MDA-435 activity of low molecular polypeptide ZY4.

1. Collect the breast cancer cell MDA-435 in the logarithmic phase to prepare cell suspension, adjust its concentration to $5 \times 10^6$-$10 \times 10^6$/ml, add 100 ul to each hole, pave the plate to adjust the cell density to 1000-10000 holes; fill the holes on the edges with sterile PBS;

2. Incubate cells under the condition of 5% CO2 and 37° C. until the cell monolayer are paved on 96-hole plate bottom; after cell adhesion for 2-12 h, add the low molecular polypeptide ZY4 at a concentration of 50-300 ug/ml, and the same volume of NS as control, to incubate for 16-48 h under the condition of 5% CO2 and 37° C., and then observe under an inverted microscope;

3. Add 20 ul of 5 mg/ml MTT solution to each hole, to continue to culture 4 h, and then draw the culture solution in the hole;

4. Add 150 ul of DMSO to each hole, place to a shaker for oscillation 10 min at a low speed, to allow the crystals fully dissolved, measure the absorbance values of each hole at OD 490 nm using a ELISA Reader; at the same time, set the zero hole and control hole. Results are shown in FIG. 4. The OD value is 0.17 when breast cancer cells MDA-435 are treated by 300 ug/ml ZY4; and OD value is 0.20 when breast cancer cells MDA-435 are treated by 200 ug/ml ZY4; OD value is 0.61 when breast cancer cells MDA-435 are treated by 100 ug/ml ZY4; and OD value is 0.7 when breast cancer cells MDA-435 are treated by 50 ug/ml ZY4, suggesting that ZY4 has a concentration-dependent effect on breast cancer cell MDA-435.

Embodiment 7: Assay on Activity of Low Molecular Polypeptide ZY4 Against Melanoma Cell A357

Figure 5:
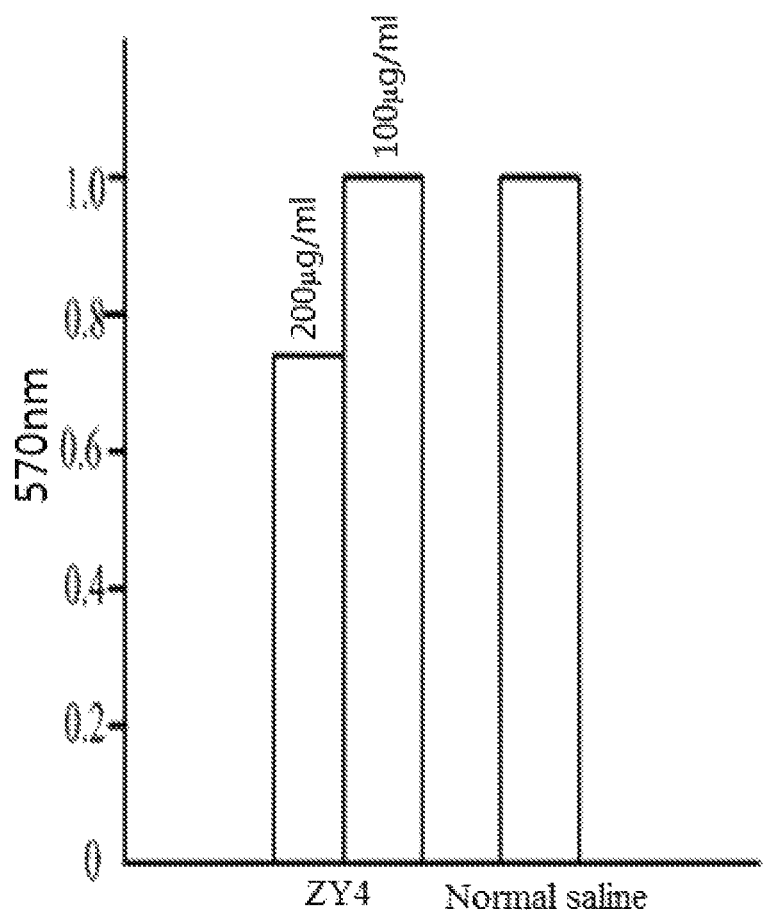
FIG. 5 is a schematic diagram of anti-melanoma cell A357 activity of low molecular polypeptide ZY4.

1. Collect the melanoma cell A357 in the logarithmic phase to prepare cell suspension, adjust its concentration to 5×10⁶-10×10⁶/ml, add 100 ul to each hole, pave the plate to adjust the cell density to 1000-10000 holes; fill the holes on the edges with sterile PBS;

2. Incubate cells under the condition of 5% CO2 and 37° C. until the cell monolayer are paved on 96-hole plate bottom; after cell adhesion for 2-12 h, add the low molecular polypeptide ZY4 at a concentration of 100 ug/ml and 200 ug/ml, and the same volume of NS as control, to incubate for 16-48 h under the condition of 5% CO2 and 37° C., and then observe under an inverted microscope;

3. Add 20 ul of 5 mg/ml MTT solution to each hole, to continue to culture 4 h, and then draw the culture solution in the hole;

4. Add 150 ul of DMSO to each hole, place to a shaker for oscillation 10 min at a low speed, to allow the crystals fully dissolved, measure the absorbance values of each hole at OD 490 nm using a ELISA Reader; at the same time, set the zero hole and control hole. Results are shown in FIG. 5. The OD value is 1.0 when melanoma cell A357 is treated by 100 ug/ml ZY4; and OD value is 0.72 when melanoma cell A357 is treated by 200 ug/ml ZY4; OD value is 1.0 when melanoma cell A357 is treated by NS, suggesting that ZY4 at a concentration of 200 ug/ml has a significant inhibitory effect on melanoma.

Embodiment 8: Assay on Activity of Low Molecular Polypeptide ZY4 Against Liver Cancer Cell HepG2

Figure 6:
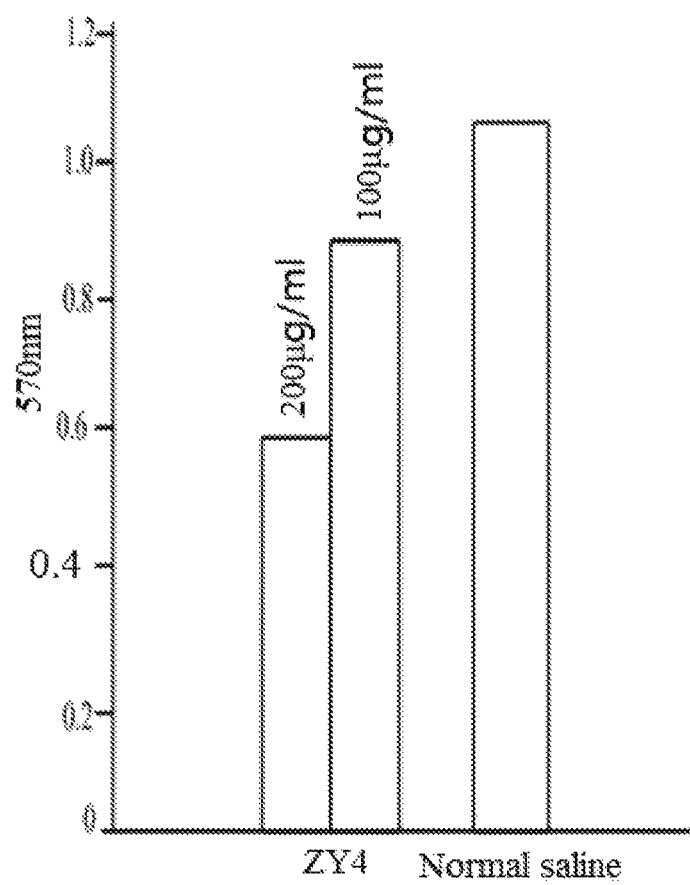
FIG. 6 is a schematic diagram of anti-hepatoma cells HepG2 activity of low molecular polypeptide ZY4.

1. Collect the liver cancer cell HepG2 in the logarithmic phase to prepare cell suspension, adjust its concentration to 5×10⁶-10×10⁶/ml, add 100 ul to each hole, pave the plate to adjust the cell density to 1000-10000 holes; fill the holes on the edges with sterile PBS;

2. Incubate cells under the condition of 5% CO2 and 37° C. until the cell monolayer are paved on 96-hole plate bottom; after cell adhesion for 2-12 h, add the low molecular polypeptide ZY4 at a concentration of 100 ug/ml and 200 ug/ml, and the same volume of NS as control, to incubate for 16-48 h under the condition of 5% CO2 and 37° C., and then observe under an inverted microscope;

3. Add 20 ul of 5 mg/ml MTT solution to each hole, to continue to culture 4 h, and then draw the culture solution in the hole;

4. Add 150 ul of DMSO to each hole, place to a shaker for oscillation 10 min at a low speed, to allow the crystals fully dissolved, measure the absorbance values of each hole at OD 490 nm using a ELISA Reader; at the same time, set the zero hole and control hole. Results are shown in FIG. 6. The OD value is 0.89 when liver cancer cell HepG2 is treated by 100 ug/ml ZY4; and OD value is 0.6 when liver cancer cell HepG2 is treated by 200 ug/ml ZY4; OD value is 1.0 when liver cancer cell HepG2 is treated by NS, suggesting that ZY4 at a concentration of 200 ug/ml has a significant inhibitory effect on liver cancer cell HepG2.

Embodiment 9: Assay on Activity of Low Molecular Polypeptide ZY4 Against Gastric Cancer Cells SGC7901

Figure 7:
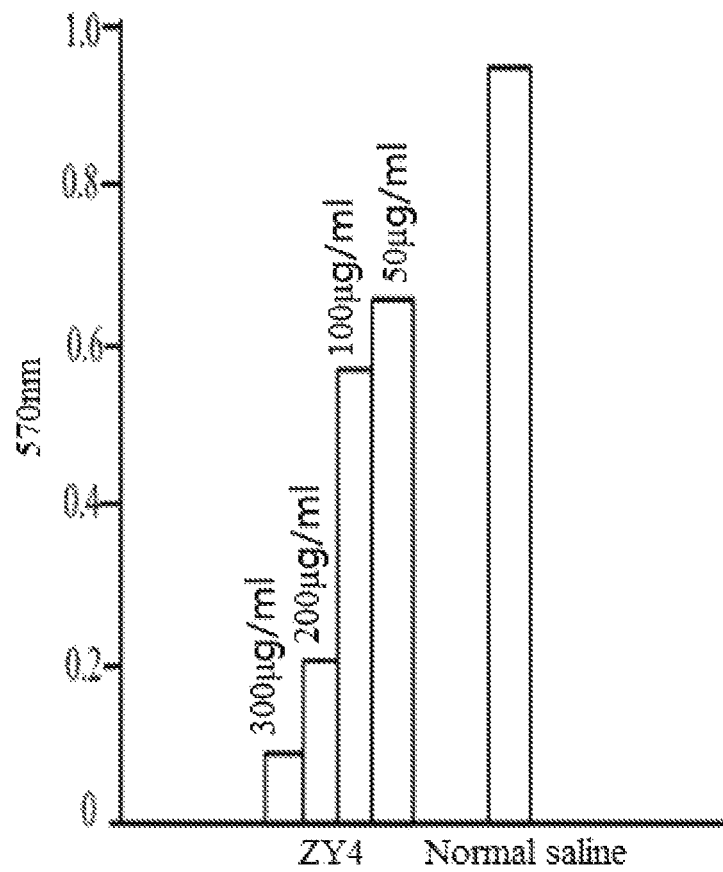
FIG. 7 is a schematic diagram of anti-gastric cancer cell SGC7901 activity of low molecular polypeptide ZY4.

1. Collect the gastric cancer cell SGC7901 in the logarithmic phase to prepare cell suspension, adjust its concentration to 5×10⁶-10×10⁶/ml, add 100 ul to each hole, pave the plate to adjust the cell density to 1000-10000 holes; fill the holes on the edges with sterile PBS;

2. Incubate cells under the condition of 5% CO2 and 37° C. until the cell monolayer are paved on 96-hole plate bottom; after cell adhesion for 2-12 h, add the low molecular polypeptide ZY4 at a concentration of 50-300 ug/ml, and the same volume of NS as control, to incubate for 16-48 h under the condition of 5% CO2 and 37° C., and then observe under an inverted microscope;

3. Add 20 ul of 5 mg/ml MTT solution to each hole, to continue to culture 4 h, and then draw the culture solution in the hole;

4. Add 150 ul of DMSO to each hole, place to a shaker for oscillation 10 min at a low speed, to allow the crystals fully dissolved, measure the absorbance values of each hole at OD 490 nm using a ELISA Reader; at the same time, set the zero hole and control hole. Results are shown in FIG. 7. The OD value is 0.65 when gastric cancer cell SGC7901 is treated by 50 ug/ml ZY4; and OD value is 0.57 when gastric cancer cell SGC7901 is treated by 100 ug/ml ZY4; OD value is 0.2 when gastric cancer cell SGC7901 is treated by 200 ug/ml ZY4, and the OD value is 0.09 when gastric cancer cell SGC7901 is treated by 300 ug/ml ZY4, suggesting that ZY4 has a significant inhibitory effect on gastric cancer cell SGC7901.

What is claimed is:

1. A low molecular weight polypeptide ZY4, comprising SEQ ID NO: 1;

wherein the SEQ ID NO: 1 has an amino acid sequence of: Valine-Cysteine-Lysine-Arginine-Tryptophan-Lysine-Lysine-Tryptophan-Lysine-Arginine-Lysine-Tryptophan-Lysine-Lysine-Tryptophan-Cysteine-Valinamide, and the two Cysteines in the amino acid sequence form an intramolecular disulfide bond.

2. A method of preparing an anti-infective drug; comprising the steps of: preparing a low molecular weight polypeptide ZY4 (SEQ ID 1) solution; administering the solution to an affected part;
 wherein the anti-infective drug has a significant inhibitory effect against at least one of *Escherichia coli, Candida albicans, Staphylococcus aureus, Bacillus subtilis, Staphylococcus haemolyticus, Staphylococcus epidermidis,* and *Staphylococcus cohnii*.

3. The method according to claim 2; wherein the low molecular weight polypeptide ZY4 (SEQ ID 1) solution has a concentration of 0.8-20 ug/mL.

4. A method of preparing an anti-acne composition, comprising the steps of: preparing an ointment comprising a low molecular weight polypeptide ZY4 (SEQ ID 1) using polyethylene glycol (PEG) and glycerol; administering the ointment to an affected part;
 wherein a mass ratio of PEG and glycerol in the ointment is 5:1.

5. The method according to claim 4, wherein a concentration of the low molecular weight polypeptide ZY4 (SEQ ID 1) in the ointment is 2 mg/mL.

6. A method of preparing a drug against lung cancer, breast cancer, melanoma, liver cancer or gastric cancer; comprising the step of: administering a low molecular weight polypeptide ZY4 (SEQ ID 1).

7. The method according to claim 6, wherein the low molecular weight polypeptide ZY4 (SEQ ID 1) has a concentration of 100 ug/mL or 200 ug/mL.

\* \* \* \* \*

SEQUENCE LISTING

```
<160> NUMBER OF SEQ ID NOS: 1

<210> SEQ ID NO 1
<211> LENGTH: 17
<212> TYPE: PRT
<213> ORGANISM: Artificial Sequence
<220> FEATURE:
<223> OTHER INFORMATION: The sequence is synthetized

<400> SEQUENCE: 1

Val Cys Lys Arg Trp Lys Lys Trp Lys Arg Lys Trp Lys Lys Trp Cys
1               5                   10                  15

Val
```